United States Patent
Corson et al.

(10) Patent No.: US 6,914,229 B2
(45) Date of Patent: Jul. 5, 2005

(54) SIGNAL OFFSET FOR PREVENTION OF DATA CLIPPING IN A MOLECULAR ARRAY SCANNER

(75) Inventors: John F. Corson, Stanford, CA (US); Debra A. Sillman, Los Altos, CA (US); Jayati Ghosh, San Jose, CA (US); Kenneth L. Staton, San Carlos, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 309 days.

(21) Appl. No.: 10/086,658

(22) Filed: Feb. 28, 2002

(65) Prior Publication Data

US 2003/0168579 A1 Sep. 11, 2003

(51) Int. Cl.[7] .............................................. H01J 40/14
(52) U.S. Cl. ............................ 250/214 R; 250/214 DC
(58) Field of Search ....................... 250/214 DC, 214 A, 250/214 R, 234; 382/133

(56) References Cited

U.S. PATENT DOCUMENTS

| | | | |
|---|---|---|---|
| 5,107,422 A | * | 4/1992 | Kamentsky et al. ........ 382/133 |
| 5,599,695 A | | 2/1997 | Pease et al. |
| 5,721,435 A | | 2/1998 | Troll |
| 5,753,788 A | | 5/1998 | Fodor et al. |
| 5,763,870 A | | 6/1998 | Sadler et al. |
| 5,786,142 A | | 7/1998 | Renfrew et al. |
| 6,171,797 B1 | | 1/2001 | Perbost |
| 6,180,351 B1 | | 1/2001 | Cattell |
| 6,232,072 B1 | | 5/2001 | Fisher |
| 6,242,266 B1 | | 6/2001 | Schleifer et al. |
| 6,323,043 B1 | | 11/2001 | Caren et al. |
| 6,329,143 B1 | | 12/2001 | Stryer et al. |
| 6,329,661 B1 | | 12/2001 | Perov et al. |
| 6,371,370 B2 | | 4/2002 | Sadler et al. |
| 6,403,957 B1 | | 6/2002 | Fodor et al. |

OTHER PUBLICATIONS

EPO Communication dated Jul. 10, 2003for EP 03251191, European Search Report on European Patent Application No. 03251191 and Annex to the European Search Report.

* cited by examiner

*Primary Examiner*—Thanh X. Luu

(57) ABSTRACT

A method and system for preventing signal clipping in a molecular array scanner by adding an offset signal to the signal generated by the photodetectors and initial stages of signal processing within a molecular array scanner in order to promote the signal above the level where signal information is lost during analog-to-digital signal conversion and/or digital signal integration. A portion of the offset is then subtracted from the digital signal or integrated digital signals, leaving a smaller, constant offset that is reported to the user, stored in a data file, or otherwise made available for further correction during later molecular array data processing.

11 Claims, 14 Drawing Sheets

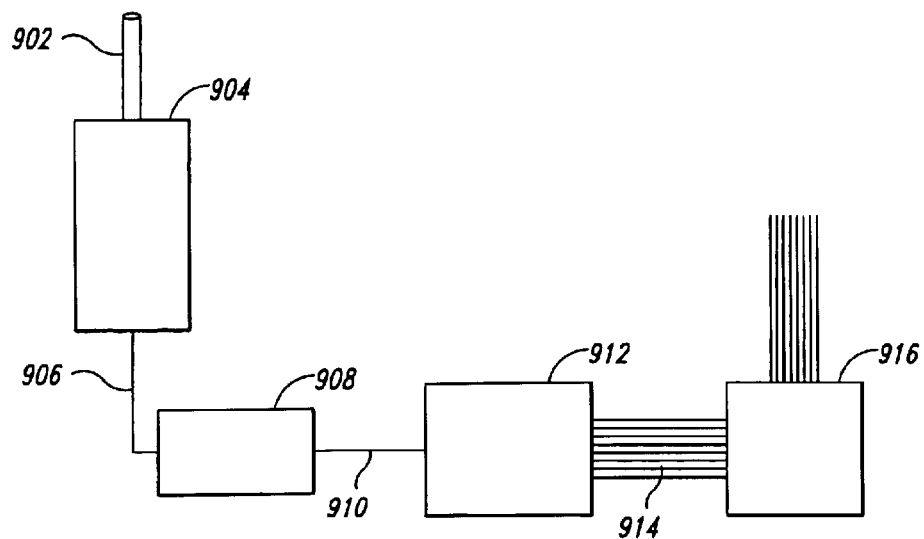
*Fig. 9*
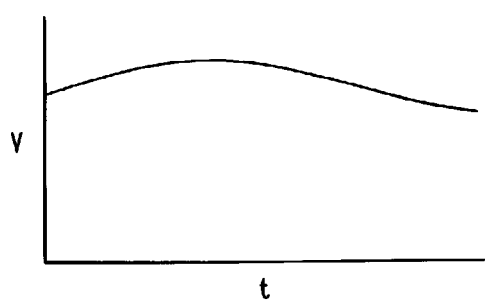 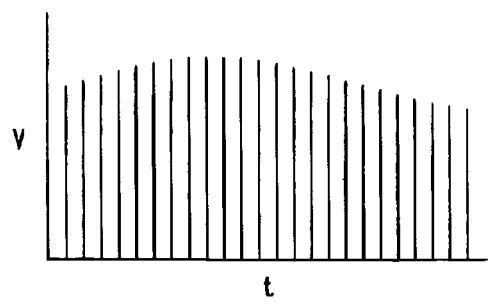
*Fig. 10A*  *Fig. 10B*

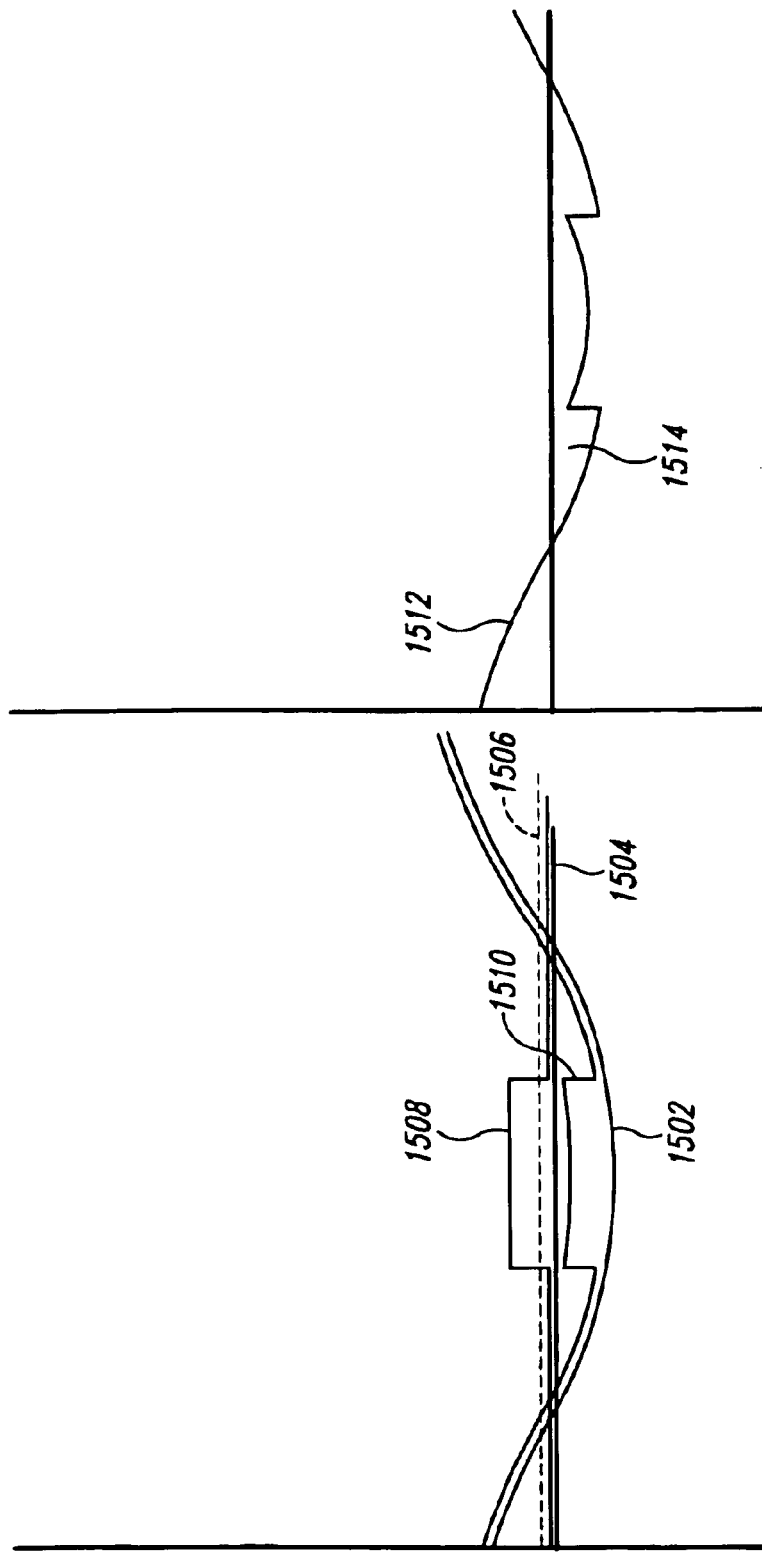

SIGNAL OFFSET FOR PREVENTION OF DATA CLIPPING IN A MOLECULAR ARRAY SCANNER

TECHNICAL FIELD

The present invention relates to molecular array scanners and, in particular, to a method and system for adding a signal offset to the signal generated during optical scanning to prevent signal loss during analog-to-digital signal conversion and signal integration.

BACKGROUND OF THE INVENTION

The present invention is related to acquisition of molecular-array data and other types of genetic, biochemical, and chemical data from molecular arrays by molecular array scanners. A general background of molecular-array technology is first provided, in this section, to facilitate discussion of the scanning techniques described in following sections.

Array technologies have gained prominence in biological research and are likely to become important and widely used diagnostic tools in the healthcare industry. Currently, molecular-array techniques are most often used to determine the concentrations of particular nucleic-acid polymers in complex sample solutions. Molecular-array-based analytical techniques are not, however, restricted to analysis of nucleic acid solutions, but may be employed to analyze complex solutions of any type of molecule that can be optically or radiometrically scanned and that can bind with high specificity to complementary molecules synthesized within, or bound to, discrete features on the surface of an array. Because arrays are widely used for analysis of nucleic acid samples, the following background information on arrays is introduced in the context of analysis of nucleic acid solutions following a brief background of nucleic acid chemistry.

Deoxyribonucleic acid ("DNA") and ribonucleic acid ("RNA") are linear polymers, each synthesized from four different types of subunit molecules. The subunit molecules for DNA include: (1) deoxy-adenosine, abbreviated "A," a purine nucleoside; (2) deoxy-thymidine, abbreviated "T," a pyrimidine nucleoside; (3) deoxy-cytosine, abbreviated "C," a pyrimidine nucleoside; and (4) deoxy-guanosine, abbreviated "G," a purine nucleoside. The subunit molecules for RNA include: (1) adenosine, abbreviated "A," a purine nucleoside; (2) uracil, abbreviated "U," a pyrimidine nucleoside; (3) cytosine, abbreviated "C," a pyrimidine nucleoside; and (4) guanosine, abbreviated "G," a purine nucleoside. FIG. 1 illustrates a short DNA polymer 100, called an oligomer, composed of the following subunits: (1) deoxy-adenosine 102; (2) deoxy-thymidine 104; (3) deoxy-cytosine 106; and (4) deoxy-guanosine 108. When phosphorylated, subunits of DNA and RNA molecules are called "nucleotides" and are linked together through phosphodiester bonds 110–115 to form DNA and RNA polymers. A linear DNA molecule, such as the oligomer shown in FIG. 1, has a 5' end 118 and a 3' end 120. A DNA polymer can be chemically characterized by writing, in sequence from the 5' end to the 3' end, the single letter abbreviations for the nucleotide subunits that together compose the DNA polymer. For example, the oligomer 100 shown in FIG. 1 can be chemically represented as "ATCG." A DNA nucleotide comprises a purine or pyrimidine base (e.g. adenine 122 of the deoxy-adenylate nucleotide 102), a deoxy-ribose sugar (e.g. deoxy-ribose 124 of the deoxy-adenylate nucleotide 102), and a phosphate group (e.g. phosphate 126) that links one nucleotide to another nucleotide in the DNA polymer. In RNA polymers, the nucleotides contain ribose sugars rather than deoxy-ribose sugars. In ribose, a hydroxyl group takes the place of the 2' hydrogen 128 in a DNA nucleotide. RNA polymers contain uridine nucleosides rather than the deoxy-thymidine nucleosides contained in DNA. The pyrimidine base uracil lacks a methyl group (130 in FIG. 1) contained in the pyrimidine base thymine of deoxy-thymidine.

The DNA polymers that contain the organization information for living organisms occur in the nuclei of cells in pairs, forming double-stranded DNA helixes. One polymer of the pair is laid out in a 5' to 3' direction, and the other polymer of the pair is laid out in a 3' to 5' direction. The two DNA polymers in a double-stranded DNA helix are therefore described as being anti-parallel. The two DNA polymers, or strands, within a double-stranded DNA helix are bound to each other through attractive forces including hydrophobic interactions between stacked purine and pyrimidine bases and hydrogen bonding between purine and pyrimidine bases, the attractive forces emphasized by conformational constraints of DNA polymers. Because of a number of chemical and topographic constraints, double-stranded DNA helices are most stable when deoxy-adenylate subunits of one strand hydrogen bond to deoxy-thymidylate subunits of the other strand, and deoxy-guanylate subunits of one strand hydrogen bond to corresponding deoxy-cytidilate subunits of the other strand.

FIGS. 2A–B illustrate the hydrogen bonding between the purine and pyrimidine bases of two anti-parallel DNA strands. FIG. 2A shows hydrogen bonding between adenine and thymine bases of corresponding adenosine and thymidine subunits, and FIG. 2B shows hydrogen bonding between guanine and cytosine bases of corresponding guanosine and cytosine subunits. Note that there are two hydrogen bonds 202 and 203 in the adenine/thymine base pair, and three hydrogen bonds 204–206 in the guanosine/cytosine base pair, as a result of which GC base pairs contribute greater thermodynamic stability to DNA duplexes than AT base pairs. AT and GC base pairs, illustrated in FIGS. 2A–B, are known as Watson-Crick ("WC") base pairs.

Two DNA strands linked together by hydrogen bonds forms the familiar helix structure of a double-stranded DNA helix. FIG. 3 illustrates a short section of a DNA double helix 300 comprising a first strand 302 and a second, anti-parallel strand 304. The ribbon-like strands in FIG. 3 represent the deoxyribose and phosphate backbones of the two anti-parallel strands, with hydrogen-bonding purine and pyrimidine base pairs, such as base pair 306, interconnecting the two strands. Deoxy-guanylate subunits of one strand are generally paired with deoxy-cytidilate subunits from the other strand, and deoxy-thymidilate subunits in one strand are generally paired with deoxy-adenylate subunits from the other strand. However, non-WC base pairings may occur within double-stranded DNA.

Double-stranded DNA may be denatured, or converted into single stranded DNA, by changing the ionic strength of the solution containing the double-stranded DNA or by raising the temperature of the solution. Single-stranded DNA polymers may be renatured, or converted back into DNA duplexes, by reversing the denaturing conditions, for example by lowering the temperature of the solution containing complementary single-stranded DNA polymers. During renaturing or hybridization, complementary bases of anti-parallel DNA strands form WC base pairs in a cooperative fashion, leading to reannealing of the DNA duplex. Strictly A-T and G-C complementarity between anti-parallel polymers leads to the greatest thermodynamic stability, but partial complementarity including non-WC base pairing may also occur to produce relatively stable associations between partially-complementary polymers. In general, the longer the regions of consecutive WC base pairing between two nucleic acid polymers, the greater the stability of hybridization between the two polymers under renaturing conditions.

The ability to denature and renature double-stranded DNA has led to the development of many extremely powerful and discriminating assay technologies for identifying the presence of DNA and RNA polymers having particular base sequences or containing particular base subsequences within complex mixtures of different nucleic acid polymers, other biopolymers, and inorganic and organic chemical compounds. One such methodology is the array-based hybridization assay. FIGS. 4–7 illustrate the principle of the array-based hybridization assay. An array (402 in FIG. 4) comprises a substrate upon which a regular pattern of features are prepared by various manufacturing processes. The array 402 in FIG. 4, and in subsequent FIGS. 5–7, has a grid-like two-dimensional pattern of square features, such as feature 404 shown in the upper left-hand corner of the array. It should be noted that many molecular arrays contain disk-shaped features, rather than round features. Each feature of the array contains a large number of identical oligonucleotides covalently bound to the surface of the feature. These bound oligonucleotides are known as probes. In general, chemically distinct probes are bound to the different features of an array, so that each feature corresponds to a particular nucleotide sequence. In FIGS. 4–6, the principle of array-based hybridization assays is illustrated with respect to the single feature 404 to which a number of identical probes 405–409 are bound. In practice, each feature of the array contains a high density of such probes but, for the sake of clarity, only a subset of these are shown in FIGS. 4–6.

Once an array has been prepared, the array may be exposed to a sample solution of target DNA or RNA molecules (410–413 in FIG. 4) labeled with fluorophores, chemiluminescent compounds, or radioactive atoms 415–418. Labeled target DNA or RNA hybridizes through base pairing interactions to the complementary probe DNA, synthesized on the surface of the array. FIG. 5 shows a number of such target molecules 502–504 hybridized to complementary probes 505–507, which are in turn bound to the surface of the array 402. Targets, such as labeled DNA molecules 508 and 509, that do not contains nucleotide sequences complementary to any of the probes bound to array surface, do not hybridize to generate stable duplexes and, as a result, tend to remain in solution. The sample solution is then rinsed from the surface of the array, washing away any unbound labeled DNA molecules. Finally, the bound labeled DNA molecules are detected via optical or radiometric scanning. FIG. 6 shows labeled target molecules emitting detectable fluorescence, radiation, or other detectable signal. Optical scanning involves exciting labels of bound labeled DNA molecules with electromagnetic radiation of appropriate frequency and detecting fluorescent emissions from the labels, or detecting light emitted from chemiluminescent labels. When radioisotope labels are employed, radiometric scanning can be used to detect the signal emitted from the hybridized features. Additional types of signals are also possible, including electrical signals generated by electrical properties of bound target molecules, magnetic properties of bound target molecules, and other such physical properties of bound target molecules that can produce a detectable signal. Optical, radiometric, or other types of scanning produce an analog or digital representation of the array as shown in FIG. 7, with features to which labeled target molecules are hybridized similar to 706 optically or digitally differentiated from those features to which no labeled DNA molecules are bound. In other words, the analog or digital representation of a scanned array displays positive signals for features to which labeled DNA molecules are hybridized and displays negative features to which no, or an undetectably small number of, labeled DNA molecules are bound. Features displaying positive signals in the analog or digital representation indicate the presence of DNA molecules with complementary nucleotide sequences in the original sample solution. Moreover, the signal intensity produced by a feature is generally related to the amount of labeled DNA bound to the feature, in turn related to the concentration, in the sample to which the array was exposed, of labeled DNA complementary to the oligonucleotide within the feature.

Array-based hybridization techniques allow extremely complex solutions of DNA molecules to be analyzed in a single experiment. An array may contain from hundreds to tens of thousands of different oligonucleotide probes, allowing for the detection of a subset of complementary sequences from a complex pool of different target DNA or RNA polymers. In order to perform different sets of hybridization analyses, arrays containing different sets of bound oligonucleotides are manufactured by any of a number of complex manufacturing techniques. These techniques generally involve synthesizing the oligonucleotides within corresponding features of the array through a series of complex iterative synthetic steps, or depositing oligonucleotides isolated from biological material.

As pointed out above, array-based assays can involve other types of biopolymers, synthetic polymers, and other types of chemical entities. For example, one might attach protein antibodies to features of the array that would bind to soluble labeled antigens in a sample solution. Many other types of chemical assays may be facilitated by array technologies. For example, polysaccharides, glycoproteins, synthetic copolymers, including block copolymers, biopolymer-like polymers with synthetic or derivitized monomers or monomer linkages, and many other types of chemical or biochemical entities may serve as probe and target molecules for array-based analysis. A fundamental principle upon which arrays are based is that of specific recognition, by probe molecules affixed to the array, of target molecules, whether by sequence-mediated binding affinities, binding affinities based on conformational or topological properties of probe and target molecules, or binding affinities based on spatial distribution of electrical charge on the surfaces of target and probe molecules.

Once the labeled target molecule has been hybridized to the probe on the surface, the array may be scanned by an appropriate technique, such as by optical scanning in cases where the labeling molecule is a fluorophore or by radiometric scanning in cases where the signal is generated through a radioactive decay of labeled target. In the case of optical scanning, more than one fluorophore can be excited, with each different wavelength at which an array is scanned producing a different signal. In optical scanning, it is common to describe the signals produced by scanning in terms of the colors of the wavelengths of light employed for the scan. For example, a red signal is produced by scanning the array with light having a wavelength corresponding to that of visible red light.

Scanning of a feature by an optical scanning device or radiometric scanning device generally produces a scanned image comprising a rectilinear grid of pixels, with each pixel having a corresponding signal intensity. These signal intensities are processed by an array-data-processing program that analyzes data scanned from an array to produce experimental or diagnostic results which are stored in a computer-readable medium, transferred to an intercommunicating entity via electronic signals, printed in a human-readable format, or otherwise made available for further use. Molecular array experiments can indicate precise gene-expression responses of organisms to drugs, other chemical and biological substances, environmental factors, and other effects. Molecular array experiments can also be used to diagnose disease, for gene sequencing, and for analytical chemistry. Processing of molecular array data can produce detailed chemical and biological analyses, disease diagnoses, and other information that can be stored in a computer-readable medium, transferred to an intercommunicating entity via electronic signals, printed in a human-readable format, or otherwise made available for further use.

An "array", unless a contrary intention appears, includes any one, two or three dimensional arrangement of addressable regions bearing a particular chemical moiety to moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, and the chemical moiety or mixture of moieties at a given feature. "Hybridizing" and "binding", with respect to polynucleotides, are used interchangeably.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features may be of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer of a type of which the features are composed). Such interfeature areas typically will be present where the arrays are formed by processes involving drop deposition of reagents but may not be present when, for example, photolithographic array fabrication processes are used,. It will be appreciated though, that the interfeature areas, when present, could be of various sizes and configurations.

The array features can have widths (that is, diameter, for a round spot) in the range from a minimum of about 10 μm to a maximum of about 1.0 cm. In embodiments where very small spot sizes or feature sizes are desired, material can be deposited according to the invention in small spots whose width is in the range about 1.0 μm to 1.0 mm, usually about 5.0 μm to 500 μm, and more usually about 10 μm to 200 μm. Features which are not round may have areas equivalent to the area ranges of round features 16 resulting from the foregoing diameter ranges.

Each array may cover an area of less than 100 cm$^2$, or even less than 50, 10 or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

FIG. 8 illustrates components of a molecular array scanner. Lasers 800*a–b* emit coherent light that passes through electro-optic modulators ("EOMs") 810*a–b* with attached polarizers 820*a–b*. Each EOM and corresponding polarizer together act as a variable optical attenuator. A control signal in the form of a variable voltage is applied to each EOM 810*a–b* by controller 880. The controller 880 may include a suitably programmed processor, logic circuit, firmware, or a combination of software programs, logic circuits, and firmware. The control signal changes the polarization of the laser light, which alters the intensity of the light that passes through the EOM. In general, laser 800*a* provides coherent light of a different wavelength than that provided by laser 810*b*. For example, one laser may provide red light and the other laser may provide green light. The beams may be combined along a path toward a stage 800 by the use of full mirror 851 and dichroic mirror 853. The light from the lasers 800*a–b* is then transmitted through a dichroic beam splitter 854, reflected off fully reflecting mirror 856, and then focused, using optical components in beam focuser 860, onto a molecular array mounted on a holder 800. Fluorescent light, emitted at two different wavelengths (for example, green light and red light) from features of the molecular array in response to illumination by the laser light, is imaged using the optics in the focuser/scanner 860, and is reflected off mirrors 856 and 854. The two different wavelengths are further separated by a dichroic mirror 858 and are passed to photodetectors 850*a–b*. More optical components (not shown in FIG. 8) may be used between the dichroic mirror and the photodetectors 850*a–b,* such as lenses, pinholes, filters, and fibers. The photodetectors 850a–b may be of various different types, including photo-multiplier tubes, charge-coupled devices, and avalanche photodiodes.

A scan system causes a light spot from each laser 800a–b to be moved in a regular pattern about the surface of the molecular array. The molecular array is mounted to a stage that can be moved in horizontal and vertical directions to position light from the lasers onto a particular region at the surface of the molecular array, from which region fluorescent emission is passed back to the photodetectors via the optical path described above. An autofocus detector 870 is provided to sense and correct any offset between different regions of the molecular array and the focal plane of the system during scanning. An autofocus system includes detector 870, processor 880, and a motorized adjuster to move the stage in the direction of arrow 896.

The controller 880 receives signals from photodetectors 850a–b, called "channels," corresponding to the intensity of the green and red fluorescent light emitted by probe labels excited by the laser light. The controller 880 also receives a signal from autofocus offset detector 870 in order to control stage adjustment, provides the control signal to the EOMs 810a–b, and controls the scan system. Controller 880 may also analyze, store, and output data relating to emitted signals received from detectors 850a–b.

The photodetectors generate an analog current signal that represents the intensity of light emitted from fluorophore or chromophore labels incorporated within probe molecules in response to excitation by the laser light. The analog current signal is first converted into an analog voltage signal before being converted into a digital voltage signal that is integrated to provide an integrated signal associated with each pixel in the scanned image of a molecular array produced by the molecular array scanner. Even when no emitted light from probe-molecule-labels are impinging on the photodetectors, the photodetectors generally produce a relatively small analog current signal, referred to below as a "no-probe" signal.

Unfortunately, converting an analog signal into a digital signal generally adds digital noise to the analog signal. Therefore, if the difference in magnitude between the no-probe signal and the analog zero current signal is small, and the digitization noise is comparable or greater in magnitude than the no-probe signal, the digitization noise may result in negative signals. Signal processing systems generally do not accept negative signals, instead setting negative numbers corresponding to negative signal intensities to digital zero. The same situation may occur for relatively weak analog signals representing relatively small emitted-light intensities detected by the photodetectors. In the case of weak analog signals, the digitization process may truncate, or clip, signal information from the optical and electronic systems of the molecular array scanner, resulting in a potential loss of information and/or distortion of the portion of the weak signal due to emitted light, or "true" signal, contained within relatively weak signals. Designers, manufacturers, and users of molecular array scanners have therefore recognized a need for a molecular array signal processing system that preserves information contained in weak signals.

SUMMARY OF THE INVENTION

One embodiment of the present invention adds an offset signal to the signal generated by the photodetectors and initial stages of signal processing within a molecular array scanner in order to promote the signal above the level where signal information is lost during analog-to-digital signal conversion and/or digital signal integration. A portion of the offset is then subtracted from the digital signal or integrated digital signals, leaving a smaller, constant offset that is reported to the user, stored in a data file, or otherwise made available for further correction during later molecular array data processing.

The present invention further provides a computer program product for use with an apparatus such as described herein. The program product includes a computer readable storage medium having a computer program stored thereon and which, when loaded into a programmable processor, provides instructions to the processor of that apparatus such that it will execute the procedures required of it to perform a method of the present invention.

BRIEF DESCRIPTION OF THE DRAWINGS

FIG. 9 shows, in block-diagram format, components of the molecular array scanner related to signal acquisition, processing and integration.

FIG. 10A shows a plot of signal intensity versus time for the analog voltage signal transmitted through signal bus 910 in FIG. 9.

FIG. 10B illustrates discrete values corresponding to the continuous analog signal shown in FIG. 10A.

FIG. 15A shows a weak measured signal as a composite of a weak true signal and a noisy background.

FIG. 15B shows the measured signal following subtraction of the average background.

FIGS. 16A–C illustrate the loss of information in a pixel-based representation of a small portion of a molecular array.

DETAILED DESCRIPTION OF THE INVENTION

Figure 1:
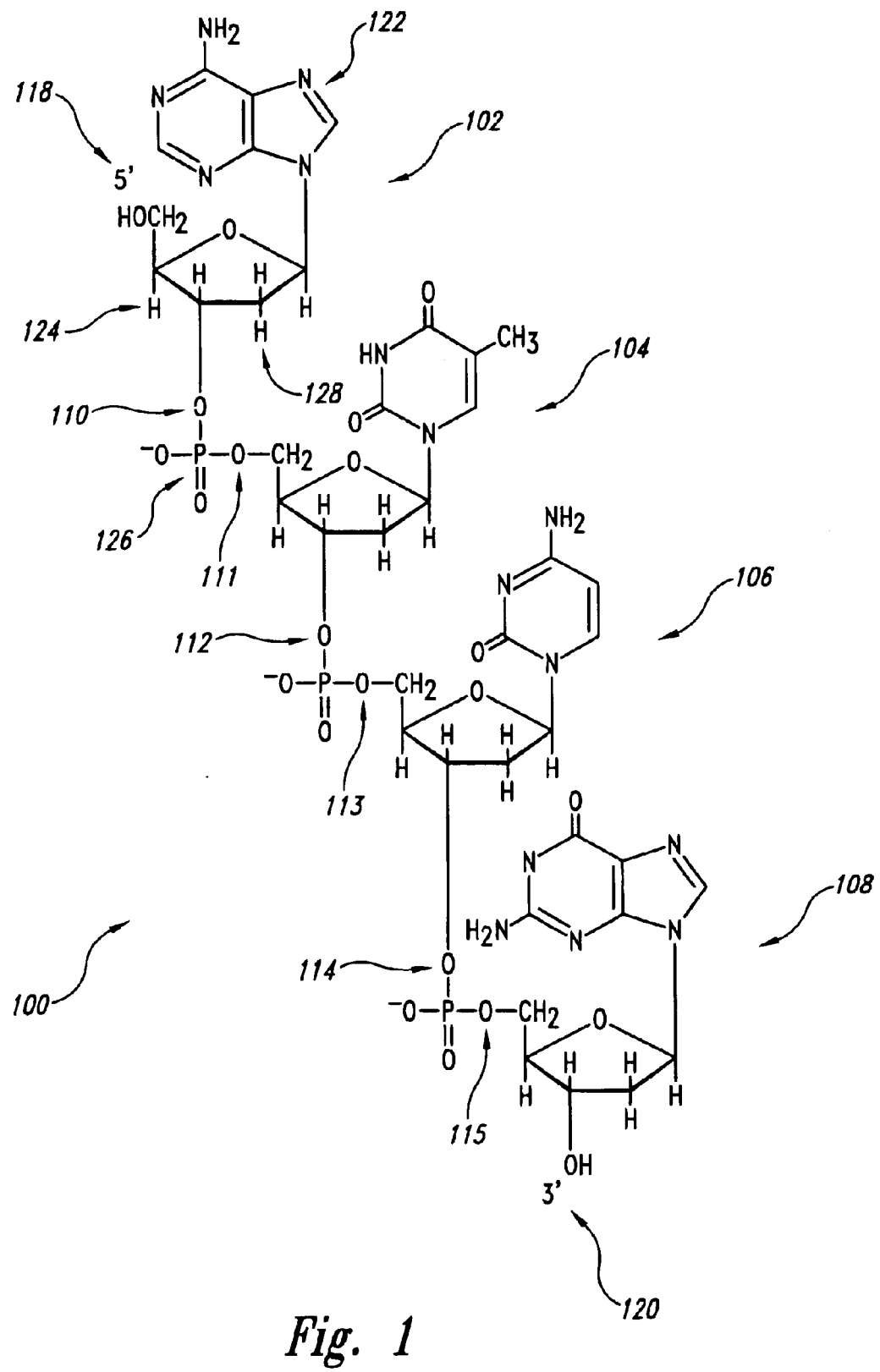
FIG. 1 illustrates a short DNA polymer 100, called an oligomer, composed of the following subunits: (1) deoxy-adenosine 102; (2) deoxy-thymidine 104; (3) deoxy-cytosine 106; and (4) deoxy-guanosine 108.
Figure 2A:
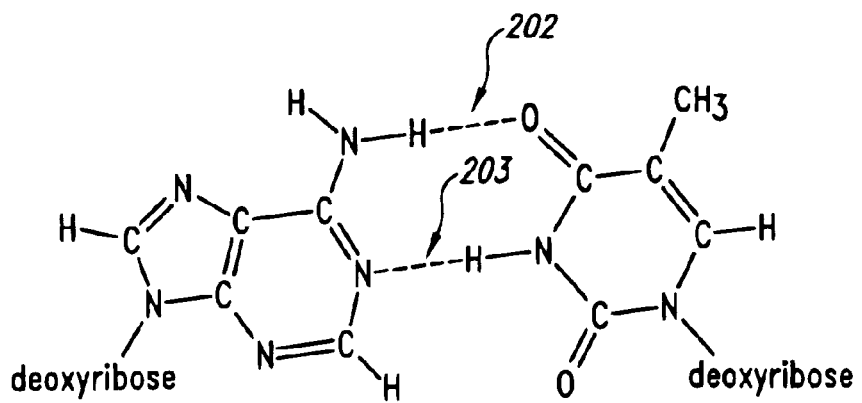
FIGS. 2A–B illustrate the hydrogen bonding between the purine and pyrimidine bases of two anti-parallel DNA strands.
Figure 2B:
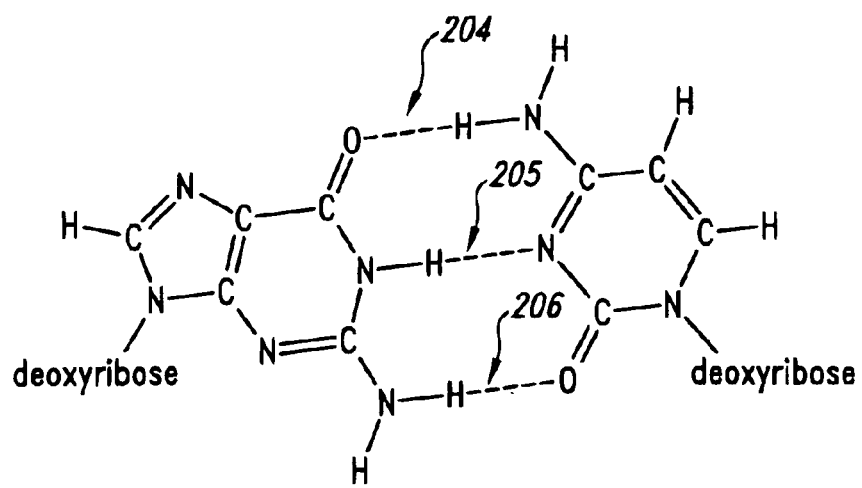
Figure 3:
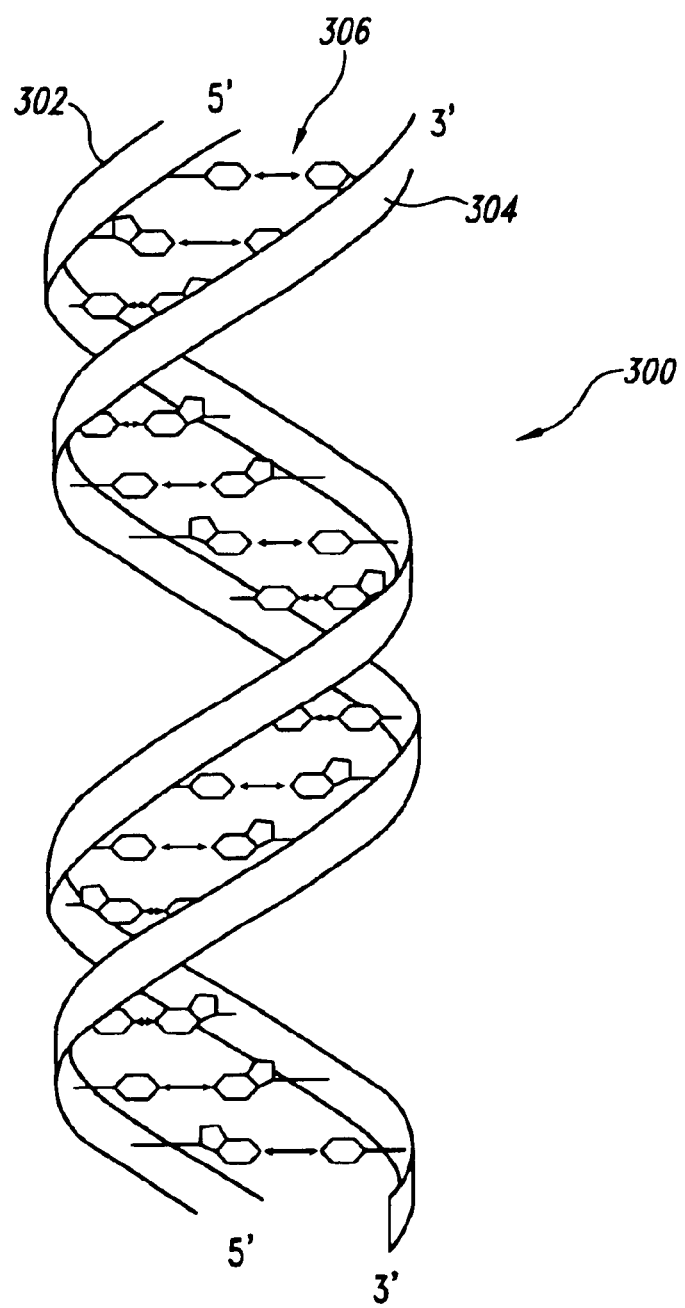
FIG. 3 illustrates a short section of a DNA double helix 300 comprising a first strand 302 and a second, anti-parallel strand 304.
Figure 4:
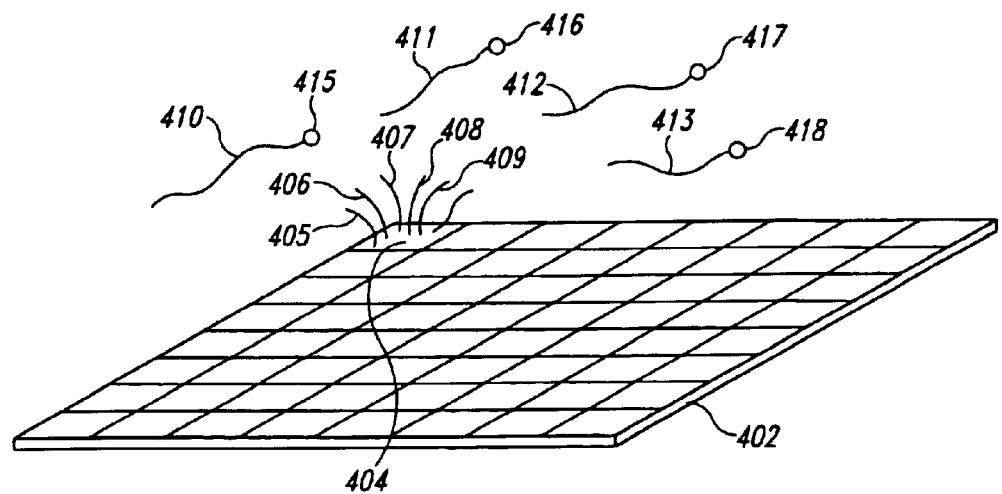
FIGS. 4–7 illustrate the principle of the array-based hybridization assay.
Figure 5:
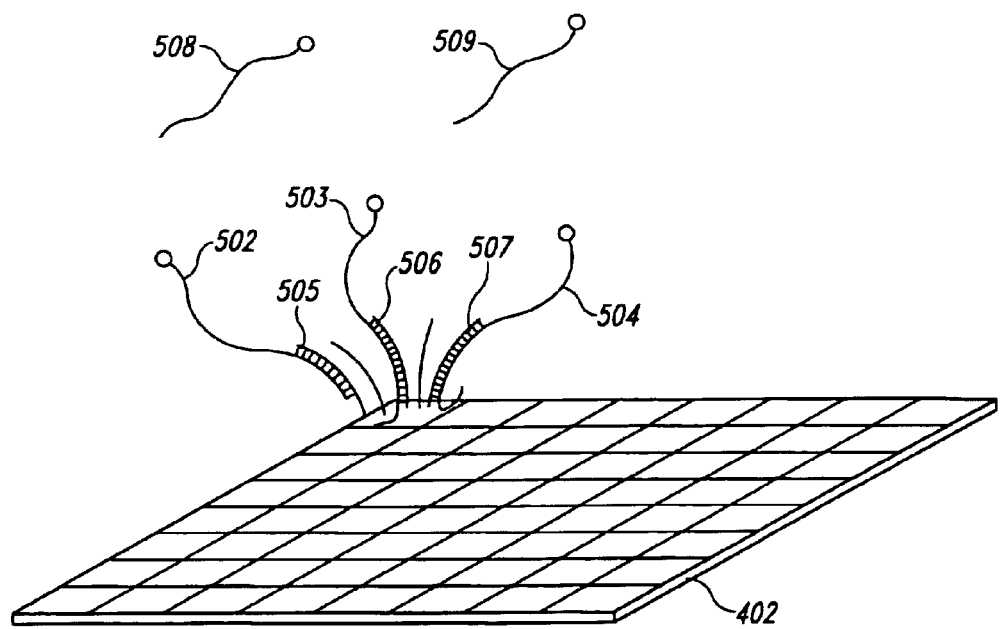
Figure 6:
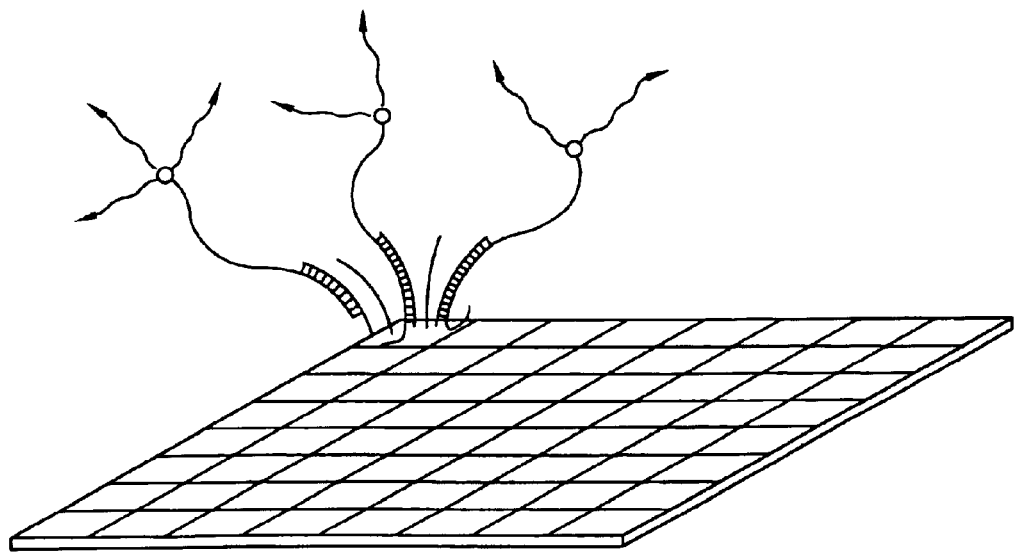
Figure 7:
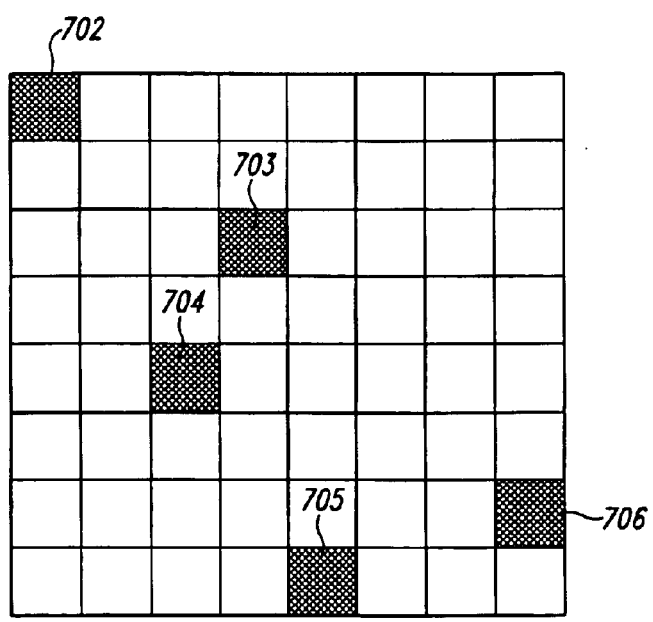
Figure 8:
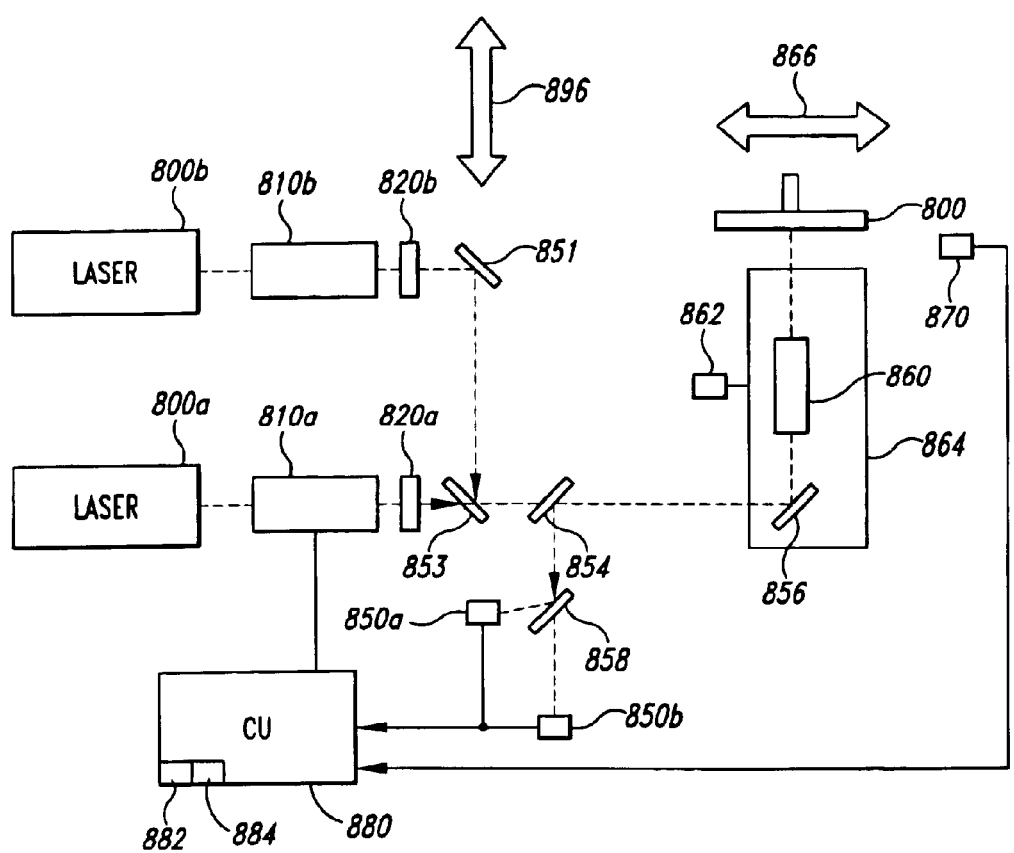
FIG. 8 is a block diagram of major optical and electronic components of a molecular array scanner.

One embodiment of the present invention is related to reliable scanning of relatively weak signals from a molecular array by a molecular array scanner. In general, strong signals are easily detected despite noise introduced by various components of the molecular array scanner. Weak signals, however, may be distorted due to truncation, or clipping, of negative values during analog-to-digital-signal conversion and/or during digital-signal integration. One embodiment of the present invention adds an offset to the signal in order to prevent signal clipping, and later removes a portion of the added offset in order to output a reliable, integrated signal that includes a small, constant offset.

FIG. 9 shows, in block-diagram format, components of the molecular array scanner related to signal acquisition, processing and integration. Light emitted by excited fluorophores or chromophores in probe molecules is optically focused onto an optical fiber, or other similar light-acquisition medium 902, for input into a photodetector 904. The photodetector produces a current signal in an output signal line 906 that is input into a current-to-voltage converter 908. The current-to-voltage converter produces an analog voltage signal in output line 910 that is input into an analog-to-digital converter 912. The analog-to-digital converter 912 outputs binary numbers via $2^n$ signal lines 914, where n is the number of signal lines and output values range from 0 to $2^n-1$. The digital signals output by the analog-to-digital converter 912 are input into a signal integrator 916 that integrates the signal over time intervals to produce a digital integrated signal for each discrete period during scanning. These time periods are adjusted to correspond to pixels of a specified dimension that correspond to regions of the surface of the molecular array. Each pixel is associated with an integer or floating point number, for each color channel used, representing the integrated scan signal from a region on the surface of the molecular array corresponding to the pixel.

FIG. 10A shows a plot of voltage versus time for the analog voltage signal transmitted through signal bus 910 in FIG. 9. The analog-to-digital converter converts the continuous analog voltage signal shown in FIG. 10A to a discrete, digital representation. FIG. 10B illustrates discrete values corresponding to the continuous analog signal shown in FIG. 10A. Thus, the analog-to-digital converter produces binary numbers at fixed intervals in time corresponding to the analog continuous signal intensity received as input via signal bus 910. In following figures, digital signals may be, at times, graphically represented as continuous function, although digital signals are actually discontinuous sequences of values, as shown in FIG. 10B.

Figure 11:
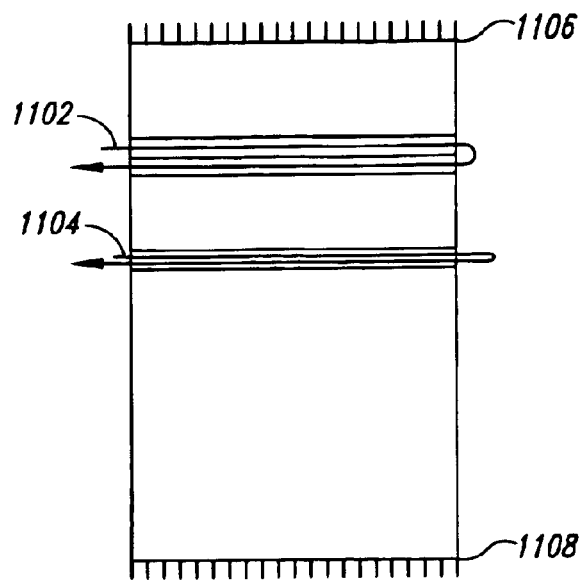
FIG. 11 illustrates scanning of a small portion of the right-hand side of a molecular array by a molecular array scanner.

FIG. 11 illustrates scanning of a small portion of the right-hand side of a molecular array by a molecular array scanner. Two different types of scans are commonly employed. In the first type of scan, the molecular array scanner scans horizontally across the array following horizontal line 1102, vertically shifts downward by a row width, and then scans back across the next row of the molecular array in an opposite direction. In the second type of scan, the molecular array scanner follows a scan path, such as scan path 1104, traversing the molecular array horizontally in one direction, reversing direction, and then re-traversing the same row of the molecular array in the opposite direction. In FIG. 11, the top 1106 and bottom 1108 edges of the portion of the molecular array are incremented. These increments correspond to the fixed integration time for the signal integrator component 916 in FIG. 9. Thus, as the molecular array scanner scans across a molecular array, a number of integrated signals are produced at regular time intervals corresponding to distance intervals across a row of the molecular array. A pixel in the scanned image of a molecular array corresponds to an area of the surface of the molecular array bound by two successive time/distance interval boundaries and the top and bottom edges of a row.

Figure 12:
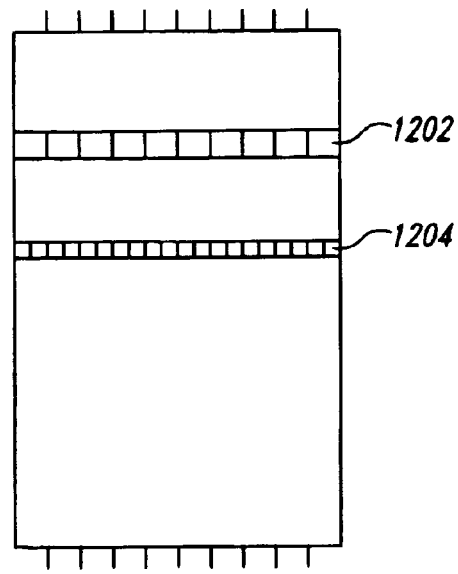
FIG. 12 illustrates output of the molecular array scanner for the portion of the molecular array shown in FIG. 11.

FIG. 12 illustrates output of the molecular array scanner for the portion of the molecular array shown in FIG. 11. When the first type of scanning method is employed (1102 in FIG. 11), large pixels, such as large pixel 1202, having a dimension equal to two times the scanning row size, are produced within a two-row horizontal stripe across the molecular array superimposed on two adjacent scan rows. When the second type of scanning procedure is employed (1104 in FIG. 11), smaller pixels, such as smaller pixel 1204, are produced in a narrower horizontal stripe across a molecular array superimposed over a single scan row. Thus, each pixel corresponds to a region of the surface of the molecular array, and is associated with an integrated signal intensity detected by a photodetector while scanning the region of the surface of the molecular array. The larger pixels, in a currently available molecular array scanner, have sides 10 microns in length, and the smaller pixels have sides 5 microns in length.

Figure 13:
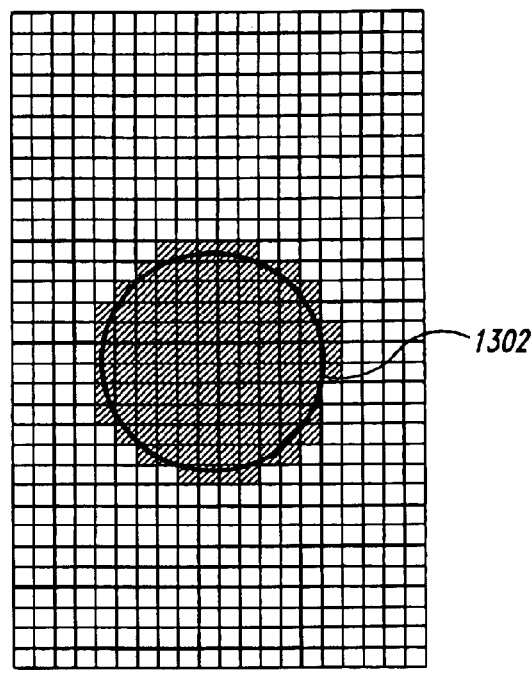
FIG. 13 illustrates the displayed, pixel-based image of the small portion of the molecular array shown in FIGS. 11 and 12.

The scanned image of a molecular array is often displayed graphically, with different colors visually encoding ranges in signal intensity. FIG. 13 illustrates the displayed image of the small portion of the molecular array shown in FIGS. 11 and 12. In FIG. 13, pixels associated with low integrated signal intensities are colorless, while pixels associated with larger integrated signal intensities are displayed as filled. The graphical display thus reveals a feature 1302 centered within the small portion of the scanned image of the molecular array.

Figure 14A:
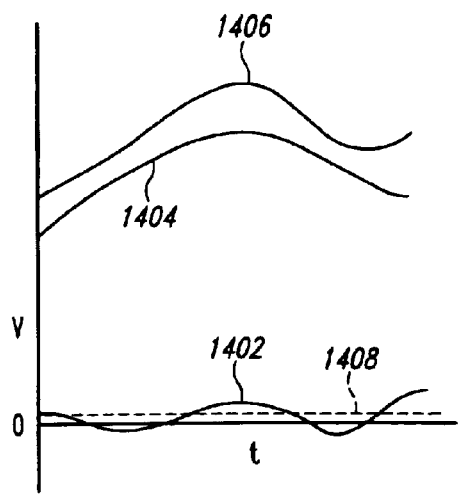
FIG. 14A shows a plot of voltage versus time of the analog voltage signal of a composite of a cumulative background and a signal proportionate to the emitted light from probe molecules.

In general, the analog signal produced by the photodetector (904 in FIG. 9) and the current-to-voltage converter (908 in FIG. 9) is a composite of various background sources and a true signal directly related to the intensity of light emitted by fluorophores or chromophores in probe molecules. FIG. 14A shows a plot of voltage versus time of the analog voltage signal of a composite of a cumulative background and a signal proportionate to the emitted light from probe molecules, or true signal. In FIG. 14A, the background 1402 is of relatively small magnitude in comparison to the true signal 1404 and the measured signal 1406 present on the signal bus 910. In FIG. 14A, an average voltage corresponding to the background is displayed as a dashed line 1408, and is roughly equal to the noise of the background shown in 1402.

Figure 14B:
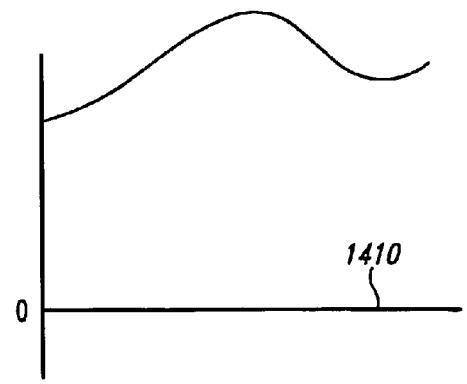
FIG. 14B displays the final output signal corresponding to the measured signal shown in FIG. 14A.

One method of processing the composite signal illustrated in FIG. 14A is to subtract the average background intensity from the measured signal 1406 to produce a final output signal. FIG. 14B displays the final output signal corresponding to the measured signal shown in FIG. 14A. Note that the final output signal shown in FIG. 14B has the same form as the measured signal shown in FIG. 14A, but is translated slightly downward toward the horizontal axis 1410 corresponding to a relative voltage potential of zero. Thus, the final signal resulting from subtraction from the average background intensity for the measured signal corresponds closely to a hypothetical true signal related to actual fluorescent emission detected by the photodetector. However, in order to perform this decomposition of the signal and the background, or some measurable portion of the background, an independent measure of the background is needed. It should also be noted that this background may be a combination of various factors, including fluorescent light from the array substrate, fluorescent light from the scanner optics, an electrical offset due to the signal processing electronics, and time-varying signals due to the light detector and related circuitry.

When the size of the background noise is comparable to, or even larger than, both the average background level and the average signal level, then the true signals can be effectively masked by background noise combined with truncation of negative voltages. This masking occurs primarily when weaker signals are processed. FIG. 15A shows a weak measured signal as a composite of a weak true signal and a noisy background. In FIG. 15A, the background 1502 fluctuates in voltage about a reference zero voltage axis 1504, with a small positive average background intensity 1506. A weak true signal 1508 rises as a square positive pulse in the middle of the horizontal axis. The measured signal 1510 that is a composite of the background 1502 and the true signal 1508 falls below the zero-voltage axis 1504 due to a large negative fluctuation in background toward the middle of the horizontal axis. FIG. 15B shows the measured signal following subtraction of the average background. The background-subtracted measured signal 1512 includes a relatively large region 1514 below the zero-voltage level.

In FIGS. 15A–B, the shape of the true signal is altered by the background noise signal fluctuations, but is still recognizable as a positive pulse. However, since the background is negative over a portion of the time shown, due, for example, to digitization noise, the clear positive pulse that characterizes the data is shifted below zero voltage. In general, regions of negative voltage in the analog signal are truncated either in analog-to-digital conversion or during signal integration. This truncation is referred to as signal clipping. Rather than output negative values, the signal integration component 916 outputs integrated signal intensities of 0 for pixels associated with negative integrated signal intensities. Thus, either during analog-to-digital signal conversion, or during digital signal integration, a portion of weak true signals may be lost. For example, although the background noise has altered the signal in FIG. 15B, the positive pulse is still visible. Once the signal below zero voltage is truncated to zero, however, the positive signal pulse effectively disappears. This is only one example of how signals can be distorted, and information lost, when the combined background level is sufficiently low digitization noise can cause the measured signal to be temporarily negative. There are many other possible ways for information to be lost, as is well-known to signal-processing engineers and molecular-array-data analysts.

Figures 16A, 16B, 16C:
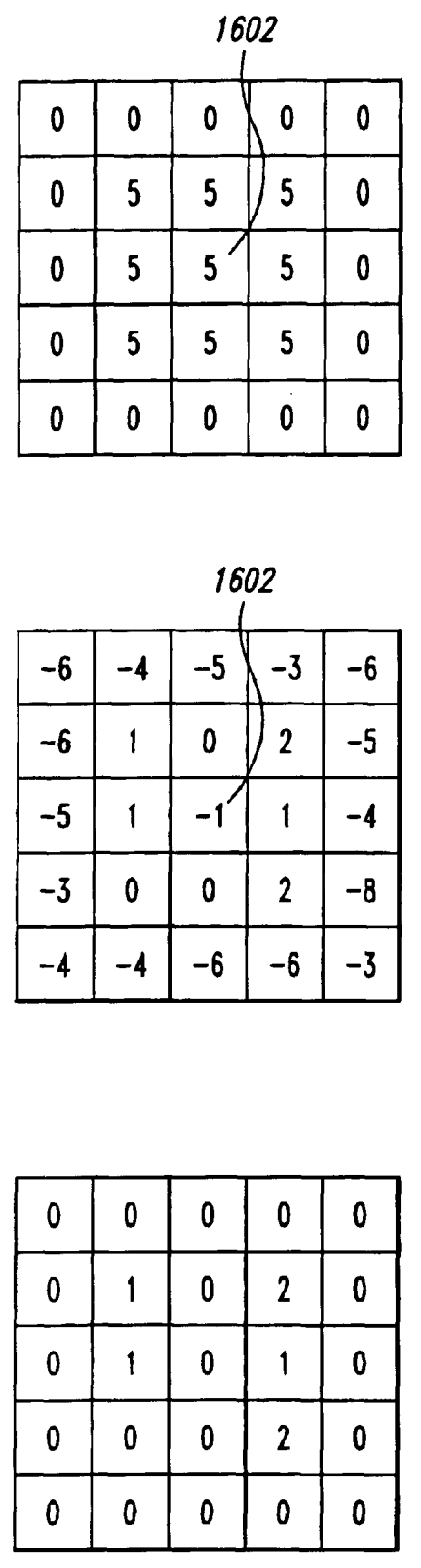

Loss of portions of weak signals may result in loss of information in the resulting pixel-based representation of the signals scanned from a molecular array. FIGS. 16A–C illustrate the loss of information in a pixel-based representation of a small portion of a molecular array. FIG. 16A shows hypothetical true integrated signal values associated with pixels in a small region of a molecular array. Note that a positive square peak occurs in the central pixels 1602. However, interference of a noisy background and subtraction of the average background intensity may result in signal clipping and zero values associated with many of the pixels near the positive square peak. FIG. 16B illustrates the small portion of an image of the molecular array shown in FIG. 16A after adding in the background. The positive square peak is still visible, no longer at positive voltage, but instead at around zero voltage. After truncating all negative voltage values to zero, as shown in FIG. 16C, the positive square peak is no longer obviously visible in the image. A scanned data processing program may easily fail to recognize the feature as a result of true signal masking.

Figure 17:
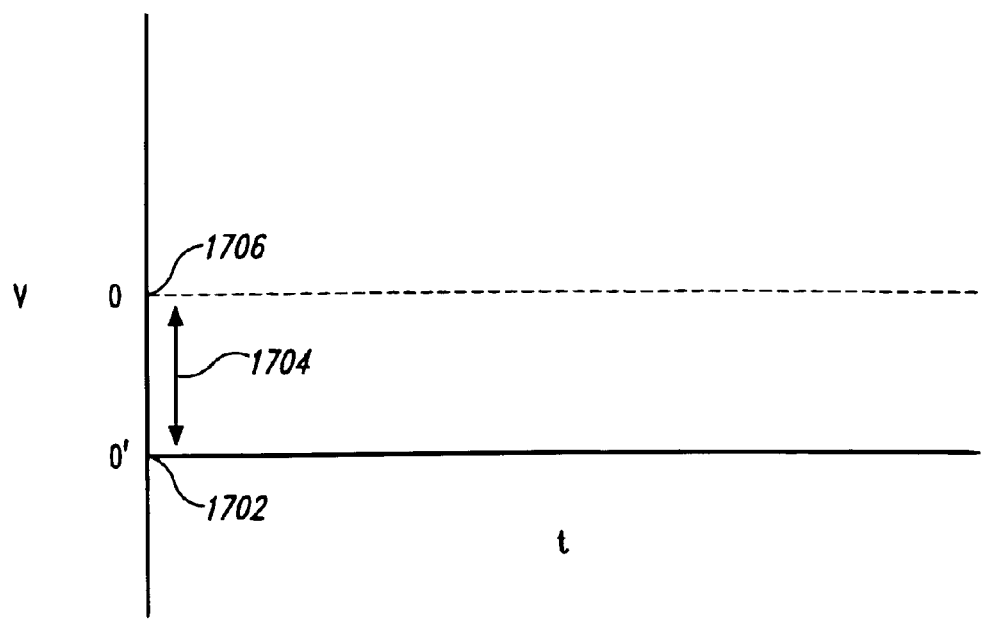
FIG. 17 illustrates addition of the offset signal to the analog voltage signal.

One embodiment of the present invention addresses the data clipping problem described above with reference to FIGS. 14–16. First, a constant offset is added to the analog voltage signal. This added offset signal can be thought of as creating a new reference voltage 0' at a lower voltage than the reference voltage 0 for the analog voltage signal without the added offset. FIG. 17 illustrates addition of the offset signal to the analog voltage signal. In FIG. 17, the new reference voltage 0' 1702 is shown displaced by an offset voltage differential 1704 from the initial reference voltage 0 1706 prior to addition of the offset.

Figure 18:
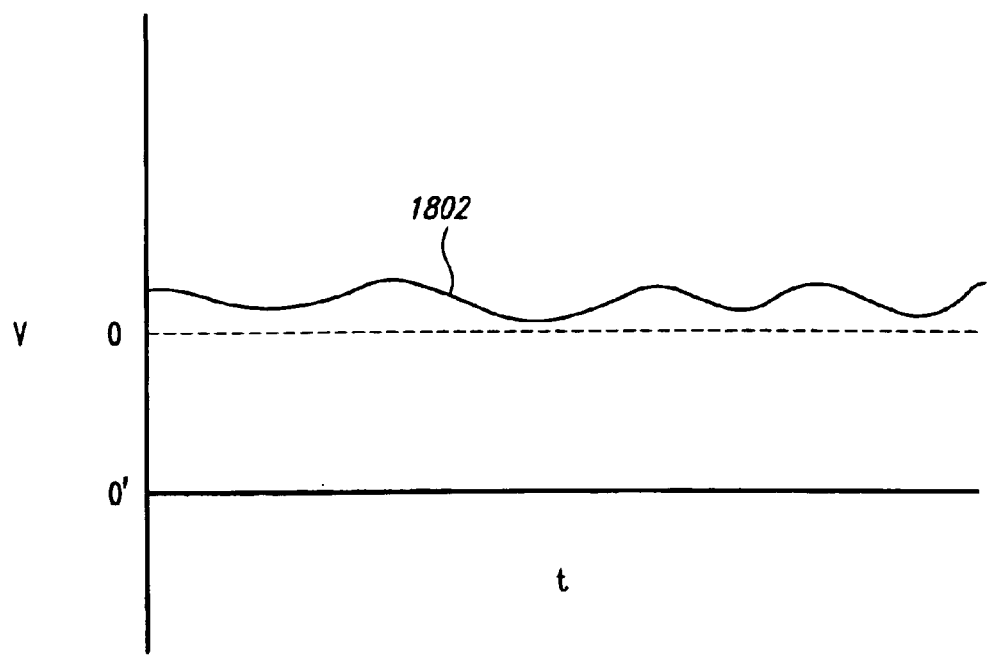
FIG. 18 illustrates the analog voltage signal generated during the dark scan over a small time period.
Figure 19:
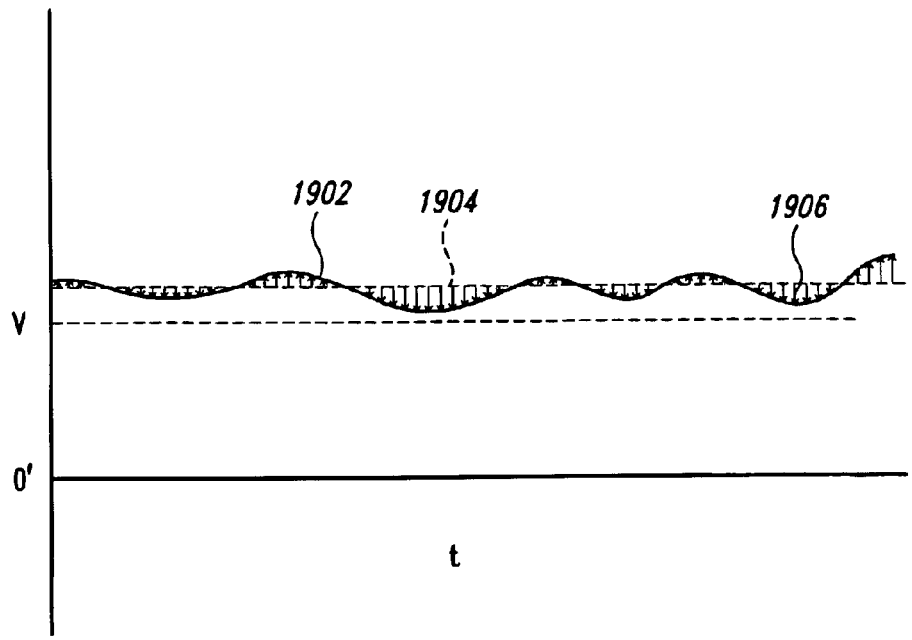
FIG. 19 illustrates the two statistical values obtained from the dark scan.

Next, the molecular array scanner is controlled to perform a "dark scan" by scanning for a period of time without a molecular array present within the molecular array scanner. The dark scan produces an analog voltage signal representative of a composite background composed from the added offset and various background sources generated by components within the optical components, the photodetector, and the signal processing electronics of the molecular array scanner. FIG. 18 illustrates the analog voltage signal generated during the dark scan over a small time period. In FIG. 18, the analog voltage signal 1802 is composed of the added offset signal along with a relatively small background component. The digital output from the dark scan is stored and processed for statistical information. Two basic statistical quantities are derived from the dark scan. The first is the mean signal intensity present during the dark scan, representing a composition of the constant offset and the background not associated with the molecular array itself. The second statistical quantity obtained by processing of the dark scan is the standard deviation of the voltage fluctuations associated with the background noise. FIG. 19 illustrates the two statistical values obtained from the dark scan. In FIG. 19, the voltage signal 1902 for a small portion, in time, of the dark scan is displayed. Note, in this discussion, actual processing of the dark-scan signal occurs following conversion to a digital signal that is stored in electronic memory accessible by software routines that process dark scan data in order to derive the statistical information illustrated in FIG. 18. The mean dark-scan signal is shown in FIG. 19 as a dotted horizontal line 1904. Fluctuations in the background intensities are shown as small vertical arrows, such as small vertical arrow 1906. The standard deviation for the fluctuations is:

$$\sigma = \sqrt{\frac{\sum_{t=1}^{n} (I_t - I_m)^2}{n}}$$

where $I_t$ is the dark-scan signal measured at a particular time t, $I_m$ is the mean dark-scan signal, and n is the number of dark-scan samples.

Figure 20:
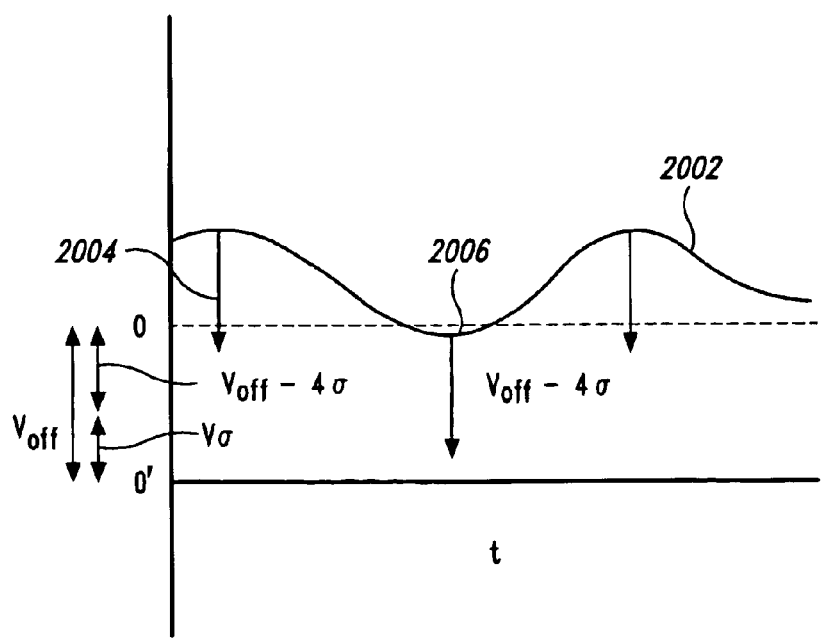
FIGS. 20–21 illustrate the offset correction employed to process scanned data.
Figure 21:
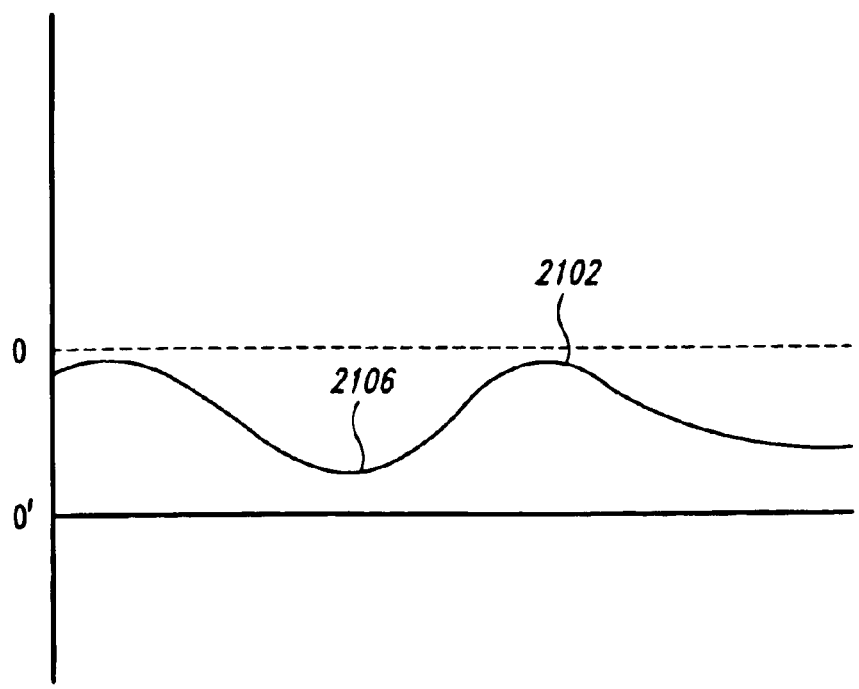

Following determination of the standard deviation for the background, the molecular array scanner can be used to scan molecular arrays for data acquisition purposes. The measured signal is then processed to remove a portion of the offset signal introduced in order to raise the total, composite signal above the reference voltage 0'. FIGS. 20–21 illustrate the offset correction employed to process scanned data. FIG. 20 shows a small portion of a measured signal 2002 that includes the added offset. The measured signal is then corrected by subtracting from the measured signal the offset signal voltage differential $V_{off}$ minus four times the standard deviation of the background noise fluctuation, $4\sigma$. Thus, each point of the measured signal 2002 is translated downward vertically by $V_{off}$–$4\sigma$, as indicated in FIG. 20 by downward vertical arrows, such as downward vertical arrow 2004. FIG. 21 shows the resulting, offset-subtracted signal 2102 with respect to the reference voltage 0' and the reference 0. Note that, in FIG. 20, the lowest point of the measured signal 2006 falls below the reference voltage 0. However, following subtraction of $V_{off}$–$4\sigma$, that lowest point (2106 in FIG. 21) lies above the reference voltage 0'. Thus, by adding the signal offset and then subtracting a portion of the signal offset following analog-to-digital conversion of the signal, almost no signal clipping occurs. In practice, subtraction of the constant $V_{off}$–$4\sigma$ for the measured signal results in clipping of fewer than one out of every million pixels in the final integrated signals produced by the molecular array scanner.

Figure 22:
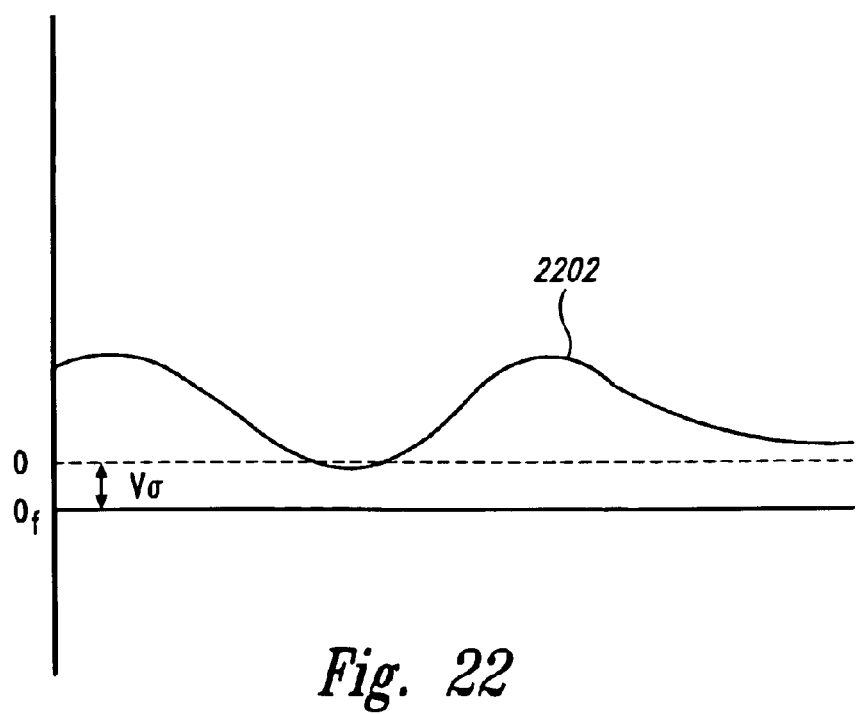
FIG. 22 illustrates the reference voltage $0_f$ that can be thought of as being produced by the above-described method.

Another way to view the process described above that represents one embodiment of the present invention is that, by adding the signal offset and then later subtracting $V_{off}$–$4\sigma$, a new reference voltage $0_f$ that is translated $4\sigma$ downward from reference voltage 0 is established. FIG. 22 illustrates the reference voltage $0_f$ that can be thought of as being produced by the above-described method. Note that the measured signal 2202 is translated vertically upward by $4\sigma$ with respect to reference voltage $0_f$ in relation to the position of the measured signal curve 2202 with respect to reference voltage 0.

Removal of a portion of the signal offset can be performed prior to signal integration, or following signal integration, by processing the resulting pixel-based scanned image to remove a portion of the integrated signal offset. The remaining offset present in the signal, $4\sigma$, can be reported to the user, included within a data file that contains the pixel-based scanned image, or otherwise made available to be used in subsequent data processing to provide a true integrated signal representative of the absolute number of label fluorophores of chromophores present within regions of the surface of the molecular array corresponding to pixels.

Although the present invention has been described in terms of a particular embodiment, it is not intended that the invention be limited to this embodiment. Modifications within the spirit of the invention will be apparent to those skilled in the art. For example, as discussed above, the offset signal can be added to the analog voltage signal, in the case that signal clipping occurs in the analog-to-digital conversion component, or added either to the analog voltage signal or to the digital signal, in the case that signal clipping occurs in the signal integration stage. Well-known electronic means can be employed to add a constant signal offset. While $V_{off}$–$4\sigma$ subtraction has been found to result in clipping of less than 1 out of a million pixels in the resulting scanned images of representative molecular arrays, subtraction of alternatively derived values may also produce acceptable results. Offset signal addition, followed by subsequent subtraction of a portion of the added offset, can be used in other types of electronic scanning and data acquisition devices, in addition to molecular array scanners. The magnitude of the offset signal depends on many different molecular-array-scanner parameters and characteristics. In general, the magnitude of the added offset signal needs to be large enough to prevent clipping, but not so large as to cause high-end signal loss or distortion.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

What is claimed is:

1. A method for reliably acquiring emitted-light intensity from the surface of a molecular array, the method comprising:

providing a probe-molecule excitation system;

providing an emitted-light photodetection system;

producing an analog signal by detecting light emitted from the surface of the molecular array;

adding a signal offset to the analog signal;

digitizing the analog signal to produce a digital signal;

subtracting a portion of the signal offset from the digital signal; and integrating the digital signal to produce integrated digital signals that are each associated with a pixel in an image of the molecular array.

2. The method of claim 1 wherein the photodetection system outputs an analog current signal that is converted to an analog voltage signal.

3. The method of claim 1 further including:

prior to detecting light emitted from the surface of the molecular array, carrying out a dark scan with no molecular array in order to determine a mean intensity and standard deviation for background generated by the photodetection system.

4. The method of claim 3 wherein the portion of the signal offset subtracted from the digital signal is the signal offset minus four times the standard deviation of the background.

5. Integrated digital signals produced by the method of claim 1 encoded by:

storing representations of the signal intensity data in a machine readable medium;

transmitting representations of the signal intensity data over an electronic communications medium;

displaying the signal intensity data on display device; and printing representations of the signal intensity data in a human readable medium.

6. A set of computer instructions for carrying out the method of claim 1 encoded by one of:

storing the computer instructions in a machine readable medium;

transmitting the computer instructions over an electronic communications medium; and printing the computer instructions in a human readable medium.

7. A molecular array scanner comprising:

a probe-molecule excitation system;

an emitted-light photodetection system that produces an analog signal representative of the emitted-light intensity;

a signal-offset adder that adds an offset to the analog signal;

an analog-to-digital converter that digitizes the analog signal to produce a digital signal;

signal-offset-subtractor logic that subtracts a portion of the signal offset from the digital signal; and a digital-signal integrator that integrates portions of the digital signal to produce integrated digital signals that are each associated with a pixel in a scanned image of the molecular array.

8. The molecular array scanner of claim 7 further including:

a memory component that stores a value that allows for calculation of the portion of the signal offset subtracted by the signal-offset-subtractor logic.

9. The molecular array scanner of claim 8 further including:

dark scan logic that controls the molecular array scanner to carry out a dark scan with no molecular array in order to determine a mean intensity and standard deviation for background generated by components within the photodetection and the signal processing systems of the molecular array scanner prior to scanning a molecular array to acquire data.

10. The molecular array scanner of claim 9 wherein the dark scan logic wherein the portion of the signal offset subtracted by the signal-offset-subtractor logic is the signal offset minus four times the standard deviation for the background.

11. Integrated digital signals produced by the molecular array scanner of claim 7 encoded by:

storing representations of the signal intensity data in a machine readable medium;

transmitting representations of the signal intensity data over an electronic communications medium;

displaying the signal intensity data on display device, and printing representations of the signal intensity data in a human readable medium.

* * * * *